United States Patent [19]

Garvey, III et al.

[11] Patent Number: 5,394,739
[45] Date of Patent: Mar. 7, 1995

[54] VISCOSITY TESTER AND METHOD WITH ORBITING OBJECT

[75] Inventors: Raymond E. Garvey, III, Powell, Tenn.; Albert C. Abnett, Nevada, Ohio; Kenneth R. Piety, Knoxville, Tenn.

[73] Assignee: Computational Systems, Inc., Tenn.

[21] Appl. No.: 254,060

[22] Filed: Jun. 6, 1994

[51] Int. Cl.[6] .................... G01N 11/12; G01N 11/14
[52] U.S. Cl. .................. 73/54.23; 73/54.18; 73/54.15
[58] Field of Search ................. 73/54.23, 54.31, 54.18, 73/54.07, 54.28, 54.15, 54.13

[56] References Cited

U.S. PATENT DOCUMENTS

| | | | |
|---|---|---|---|
| 2,957,338 | 10/1960 | Kennedy et al. | 73/54.23 |
| 3,073,150 | 1/1963 | Fann | 73/54 |
| 3,239,325 | 3/1966 | Roberson et al. | 65/162 |
| 3,677,070 | 7/1972 | Norcross | 73/57 |
| 3,836,333 | 9/1974 | Mintz | 23/259 |
| 4,388,823 | 6/1983 | Garnaud et al. | 73/57 |
| 4,448,060 | 5/1984 | Maruhnic | 73/54.18 |
| 4,627,272 | 12/1986 | Wright | 73/57 |
| 4,643,021 | 2/1987 | Mattout | 73/59 |
| 4,864,849 | 9/1989 | Wright | 73/57 |

FOREIGN PATENT DOCUMENTS

| | | | |
|---|---|---|---|
| 222122 | 5/1985 | Germany. | |
| 1-262438 | 10/1989 | Japan. | |
| 0133089 | 9/1951 | Sweden | 73/59 |
| 0148960 | 1/1962 | U.S.S.R. | 73/54.18 |
| 672543 | 7/1979 | U.S.S.R. | |
| 1168824 | 7/1985 | U.S.S.R. | |
| 1272181 | 11/1986 | U.S.S.R. | |
| 1642322 | 4/1991 | U.S.S.R. | |
| 1672303 | 8/1991 | U.S.S.R. | |
| WO91/14168 | 9/1991 | WIPO. | |

OTHER PUBLICATIONS

Brookfield TT200 Process Viscometer brochure, Brookfield Engineering Laboratories, Inc., 4 pp., Jul. 1992.
"We're put to the test thousands of times a day", Baroid Testing Equipment advertising reprint, 1 p., undated.
Solutions for Viscosity Measurement & Control advertising leaflet, Cambridge Applied Systems, Inc., 5 pp., undated.
"VISGAGE ®" brochure, Louis C. Eitzen Co., 4 pp., undated.
Rotary Viscometers brochure, Bulletin 2990, Cannon Instrument Company, 6 pp., undated.
Laboratory Equipment for Viscosity Measurement 1992.1993 catalog (39 pp.) and price list (4 pp.), Canon Instrument Company, Mar. 1992.
The Cannon Standard, a Newsletter for Viscosity Measurement brochure, vol. 4, No. 1, Cannon Instrument Company, 4 pp., Spring 1992.
CT-1000 Constant Temperature Bath leaflet, Cannon Instrument Company, 2 pp.
Cannon Rotary Viscometers, Cannon Instrument Co., 1992.
Baroid Model 35 Viscometer, Baroid Testing Equipment, 1990.
Visage Pocket Viscosity Comparator, Louis C. Eitzen Co., 1990.
Cannon Lab Equipment for Viscosity Measurement, Cannon Instrument Co., 1992–1993.
The Cannon Standard—A Newsletter for Viscosity Measurement, Cannon Instrument Co., 1992.
Cannon CT-1000 Constant Temperature Bath, Cannon Instrument Co., 1992.

*Primary Examiner*—Hezron E. Williams
*Assistant Examiner*—J. David Wiggins
*Attorney, Agent, or Firm*—Luedeka, Neely & Graham

[57] ABSTRACT

A viscosity tester includes a free standing magnetic object disposed in fluid in a stationary receptacle. A magnetic force drives the object in an orbit and the magnetic force, the speed of the object and the lag angle between the magnetic field and the object are either measured or controlled and, based on at least one of these three parameters, the viscosity of the fluid is determined. In one embodiment, a magnetic ball is driven by four electromagnets, with proximity sensors detecting the presence of the ball and controlling the electromagnets. In another embodiment, a free standing magnet is driven in an orbital pattern by a rotating field that is coaxial with the orbital pattern and is produced by a rotating magnet or a stator.

30 Claims, 9 Drawing Sheets

VISCOSITY TESTER AND METHOD WITH ORBITING OBJECT

BACKGROUND OF THE INVENTION

The present invention relates generally to the measurement of fluid viscosity and more particularly to a viscosity tester which orbits a free standing object (e.g., one for which the top portion is not constrained) through fluid placed in a testing cup and, sensing movement of the object around the cup, provides data from which the viscosity may be calculated.

The accurate measurement of the viscosity of a fluid is important in a variety of commercial and scientific endeavors. Accordingly, a number of viscosity testers and testing methods have been developed, with the goal being a viscosity measurement that can be done quickly and which produces accurate and repeatable results for fluids having a wide range of viscosities. Unfortunately, the prior art has not fully met this goal.

One measurement technique that has been tried repeatedly in the prior art is to cause the movement of an object through the fluid to be tested under conditions whereby the speed or velocity of the object can then be determined. If proper computational techniques are used, the viscosity of the fluid can then be calculated from the velocity measurement.

Thus, for example, the viscometer disclosed in U.S. Pat. No. 4,864,849 moves a ferromagnetic bob in a reciprocating linear fashion through a tube which, in fact, is intended to be part of and not easily removable from an oil lubrication system. Thus, the device of the '849 patent is not adapted for efficient measurement of fluid viscosity in a shop or in applications where a number of different fluid samples must be checked.

The invention of Russian Invention Certificate No. 1,272,181 measures the viscosity of plastic media, particularly concrete mixtures, by placing in rotary motion a vessel containing a ball, within the mixture to be measured. A rotating magnetic field moves the ball through the mixture in a spiral trajectory having a diameter limited by the interior surface of the cylindrical vessel. The amount of time required for the ball to travel a predetermined path is then measured and from which viscosity is calculated. An apparent shortcoming of the Russian '181 viscometer is that it relies on actual mechanical movement of a rotating vessel in conjunction with a non-linear movement of the ball to produce the data from which viscosity is calculated. It requires two sensors, measures only the time of a partial revolution, and does not repetitively detect speed of the ball. The two sensors are placed in the plane and pitch of the spiral trajectory of the falling ball, and the speed of the ball is measured along an arc as it falls by the sensors. Also, there is no teaching of a testing method or apparatus which would be applicable to fluids having a wide range of viscosities, including non-plastic media.

The invention of U.S. Pat. No. 4,643,021 measures the viscosity of blood by constraining a cylinder at both ends, immersing the cylinder within a close fitting chamber surrounded by fluid, applying known torques to the cylinder through a magnetic field, and measuring the resulting speed of the cylinder at each torque level. The test chamber is confined at the top, bottom, and outside diameter. This precludes rapid removal and cleaning of the cylinder or chamber except by flushing with solvent. This invention is uniquely intended for low viscosity biological fluid such as blood.

What is needed, then, is a low cost, rapid, simple viscosity tester and method which can easily and quickly be used in the shop or field or laboratory or in-line to measure the viscosity of fluids having a wide range of viscosities and which does so with good repeatability, reasonable accuracy, small sample volume, and solvent free cleaning. Such a device is lacking in the prior art.

SUMMARY OF THE INVENTION

An object of the viscosity tester of the present invention is to allow for accurate testing of the viscosity of fluids over a wide viscosity range, and especially to rapidly test multiple samples in a simple, rugged, compact device suitable for field use requiring ease of filling, testing, and cleaning either with or without use of cleaning solvents.

A further object of the viscosity tester is to provide a method of measuring viscosity which is relatively independent of frictional-and other drag forces caused by turbulent fluid flow or by contact between an object being moved and the test vessel containing the fluid.

A further object of the present invention is to provide a viscosity tester which has no moving parts except for a free standing (e.g., no physical or magnetic bearing on top portion and no brushes or other physical electrical connections) testing object moving in the fluid.

Another object is to provide accuracy by repetitively measuring the speed by counting many orbital circuits of the object in a fluid to derive an accurate measure of speed.

Another object is to provide accuracy by measuring temperature and heating the fluid with heat from electromagnets to achieve a desired temperature.

Another object is to control the magnetic force that moves a testing object through fluid to maintain laminar flow.

Another object is to control or measure (1) the magnetic force (or power) on a moving object in a fluid, (2) the speed of the moving object, and (3) the lag between the magnetic force and the object; whereby viscosity is typically determined by knowing or controlling two of these and then measuring the third.

Another object of the present invention is to measure the viscosity of a fluid by repeatable and consistent electromagnetic orbiting of a testing ball around the inside diameter of a fluid testing cup.

Still another object of the present invention is to provide a viscosity tester where the testing fluid and cup can be easily removed from the tester and disposed of.

These and related objects of the invention are achieved in a viscosity tester in which a test cylinder incorporates a cup chamber which receives a removable testing cup. The fluid sample to be tested is placed in the test cup along with a magnetic ball. An electromagnet assembly has multiple and separately operable electromagnets spaced around the cup chamber. The electromagnets are sequentially activated by a switched, constant current magnet driver circuit, thereby inducing and constantly controlling the lag angle between the ball and the driving electromagnet coil as the ball moves in a circular rotation around the inside of the cup. A sensor circuit includes multiple sensing coils arranged in a circular pattern below the testing cup. Proximity detectors generate a series of ball position indicating signals or pulses as the ball passes through a proximity sensing field corresponding to each sensing coil. The proximity sensing fields of adjacent sensing coils may overlap to prevent magnetic field dead zones in the testing cup. In this embodiment, the proximity detectors control the advance of the switching electromagnets. In this way, lag angle and power are consistent while ball speed varies with changing viscosity.

A microprocessor located on a processor board in the tester times the pulses coming from the sensor circuit, such pulses being indicative of the velocity of the ball through the fluid. The current from the magnet driver circuit is controlled by modulation of the width of pulses from the microprocessor and adjusted when necessary by the processor to maintain the velocity of the ball within a range where laminar flow conditions predominate within the sample fluid.

A magnet switching circuit receives and processes the position indicating signals from the sensor circuit in a manner whereby when the test ball moves into the proximity of said sensing field, the next sequential electromagnet is activated.

Fluid temperature monitoring means are also provided. The electromagnet assembly can also be used to heat up the fluid or, in connection with the testing ball, stir it before the test procedure has begun. A video display and serial data interface communicate the test results and the latter connects them to a separate computer where further calculations can be made or from which tester control signals can be generated.

In accordance with a more general aspect of the invention, the apparatus for measuring the viscosity of a fluid includes a stationary receptacle for containing the fluid, and a free standing magnetic object is disposed in the fluid in the receptacle. By magnetic object we are referring to any object capable of being attracted by a magnetic field. A magnet arrangement, which is preferably a microprocessor controlled electromagnet arrangement, produces and imposes a magnetic force on said magnetic object and moves the object through said fluid in a generally orbital pattern in said receptacle to produce at least one parameter corresponding to the viscosity of the fluid. The preferred orbital pattern is a circle, but other symmetrical patterns such as an ellipse and non-symmetrical patterns are also considered orbital patterns. Also, an object rotating on its axis is considered a special case of an orbital pattern, as used herein, since the off-axis portions of the object follow an orbit that will perform the desired function in some embodiments of the present invention as described in more detail below. A sensor detects the parameter referenced above and produces a signal corresponding to the viscosity of the fluid.

In one embodiment, the measured parameter corresponds to speed of the magnetic object. In this case, the sensor includes at least one position sensor for sensing the magnetic object at a sensed position as the magnetic object moves in the generally orbital pattern and for advancing the controlled magnetic field ahead of said magnetic object. As the object orbits, it repetitively passes the sensed position, and the sensor repetitively produces a position signal that corresponds to the speed of the magnetic object and the viscosity of the fluid. Thus, the parameter being sensed is the speed of the magnetic object. A processor, preferably a microprocessor, receives the position signal and counts each time the object passes the sensed position during a predetermined period of time. By this process, the processor produces a count corresponding to the number of times the magnetic object completes the orbital pattern during said period of time. This count corresponds to the speed of the object and the viscosity of the fluid. Preferably, the processor converts the count directly to a viscosity using a calibrated look-up table that associates counts with viscosities.

DESCRIPTION OF THE PREFERRED EMBODIMENT

Figure 1:
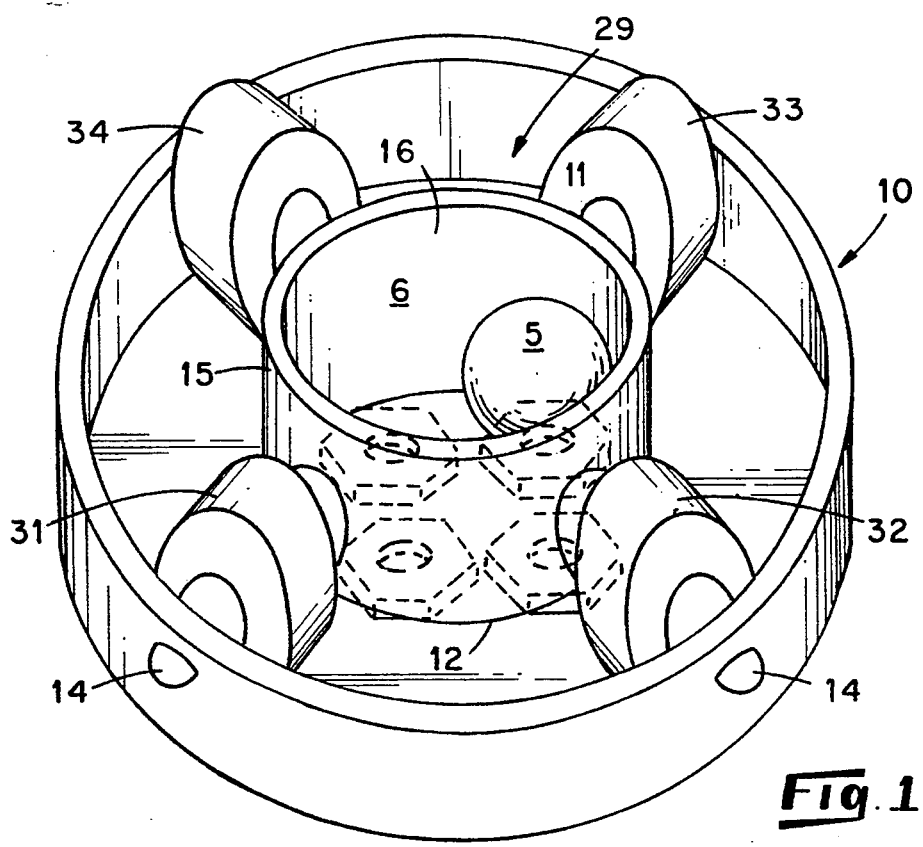
FIG. 1 is a somewhat diagrammatic oblique view looking from the top of the viscosity tester, with the sensing coils shown in phantom below the test cylinder.

In one embodiment, the viscosity tester of the present invention is incorporated in a free standing unit which is used in conjunction with a testing cup which is easily removable. In an alternate preferred embodiment, the testing cup is formed as an integral and permanent part of the tester. Accordingly, looking at FIGS. 1, 2, and 3, the viscosity tester has a test cylinder 10 formed of a cylindrical wall 11 and circular base 12 leaving centrally disposed therein a cylindrical cup chamber 15 defined by a chamber side wall 16 and circular chamber bottom wall 17. The size and precise geometry of cup chamber 15 can vary but should closely conform to the shape of test cup 6. Test cup 6 and test cylinder 10 should be manufactured in a generally cylindrical shape from a non-metallic material so that a steel or other magnetic test ball 5 can be detected through the cup with sensors such as sensing coils L5–hereinafter described. In an embodiment of the viscosity tester, test cylinder 10 has an upper surface 13 which tapers inwardly and down to chamber side wall 16 whereby the junction of upper surface 13 and chamber side wall 16 define a fill line 29. As shown in FIG. 3, the tester may be used with or without a removable cup 6, which is shown in position above the cylinder 10 for being inserted into the cylinder 10. The cup 6 is dimensioned to fit snugly in cylinder 10 and extend above the fill line 29. As shown in FIG. 3, a temperature sensor 7 is embedded in the bottom wall 17 of the test cylinder 10 for determining the temperature of fluid as hereinafter discussed.

Figure 2:
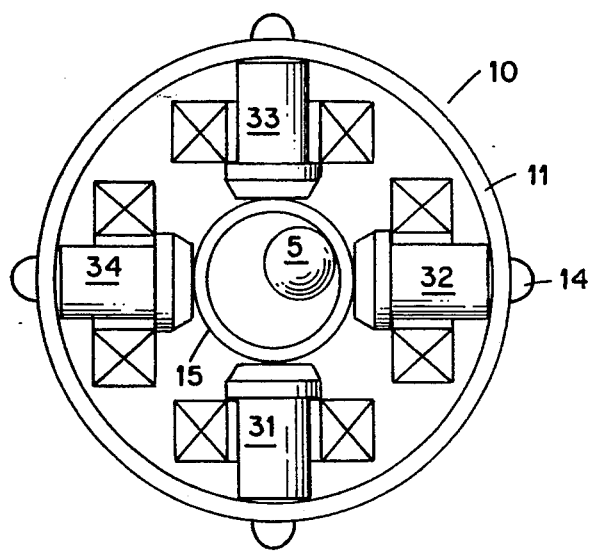
FIG. 2 is a somewhat diagrammatic plan view of the viscosity tester.
Figure 3:
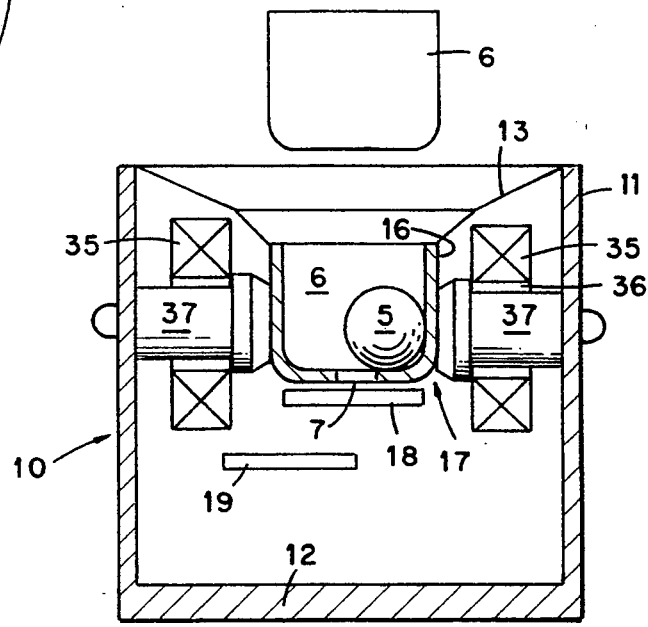
FIG. 3 is a somewhat diagrammatic cut away side view of the viscosity tester of FIG. 2 with a removable cup disposed above the cylinder.

As best seen on FIGS. 1 and 2, an electromagnet assembly (30 on FIG. 5) includes multiple electromagnets 31, 32, 33, and 34 equally spaced around the interior of test cylinder 10, being mounted to test cylinder wall 11 by magnet attachment screws 14. Preferably, there are at least four electromagnets whereby each quadrant of cup chamber 15 is within a magnetic field created by at least one activated electromagnet 31, 32, 33, or 34.

Electromagnets 31, 32, 33, and 34 are of generally conventional design, and are, for example, a coil 35 having 400 turns of 26 gauge varnished copper wire wound around an annular insulating bobbin 36, ½ in. diameter, which surrounds a magnetic polepiece 37. Of course, the dimensions of the electromagnets 31, 32, 33, and 34 will vary depending on the application. The inner facing surface of polepiece 37 is placed proximate to or is actually part of side wall 16 of cup chamber 15 so that the interior of testing cup 6, when placed in the viscosity tester, will be fully exposed to the magnetic fields of electromagnet assemblies 31, 32, 33, and 34.

Figure 4:
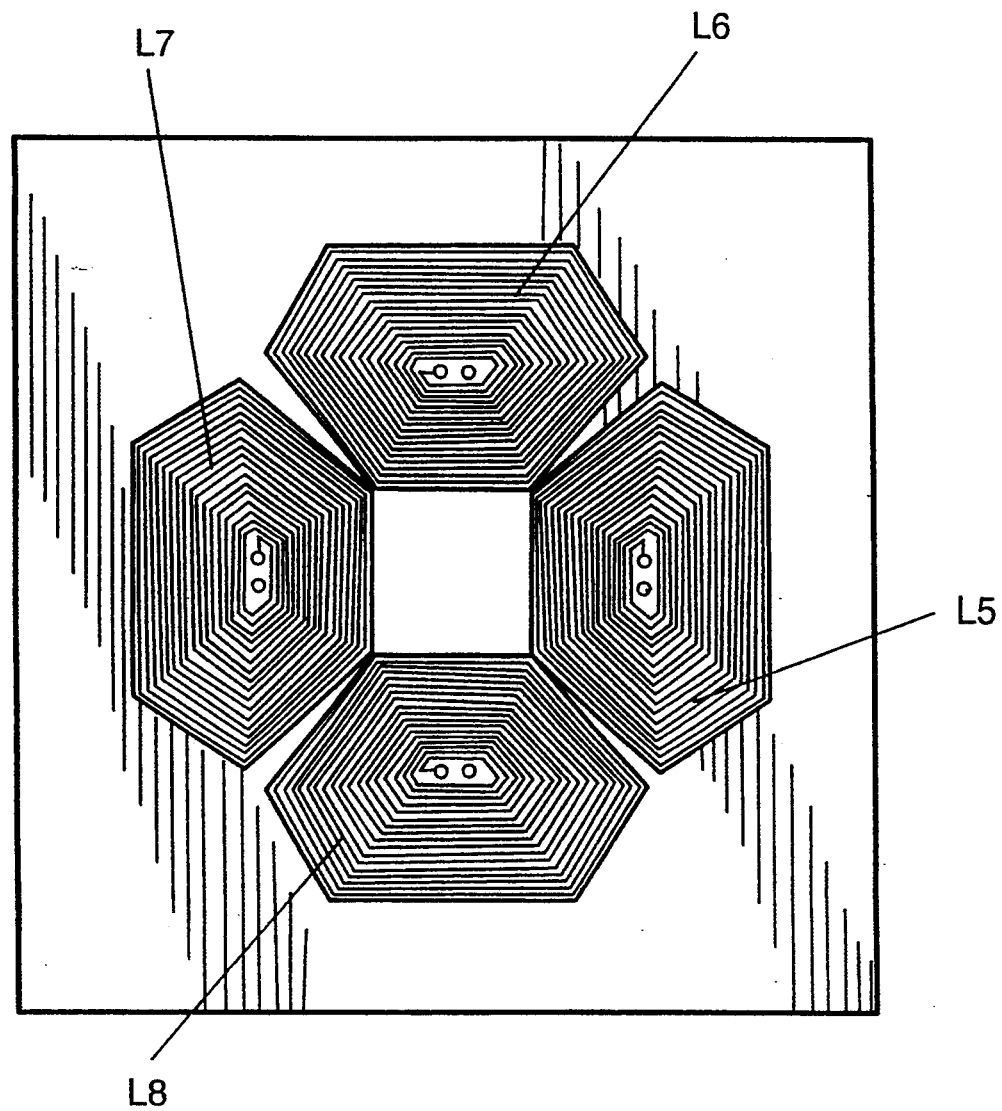
FIG. 4 is a plan view of the sensing coils of the viscosity tester mounted on the sensor printed circuit board.

A sensor printed circuit board 18 is mounted within test cylinder 10 and horizontally oriented proximate to and immediately below bottom wall 17 of cup chamber 15. A plurality of sensing coils L5, L6, L7, and L8, as shown in phantom on FIG. 1, and as seen also on FIG. 4, are mounted on sensor board 18 so that they are magnetically in close proximity to movement of ball 5 within testing cup 6. A second printed circuit board 19 is mounted below sensor board 18, to support and interconnect the processor and other electronic components and subsystems of the tester, as described below.

It can be seen from the orientation of electromagnets 31, 32, 33, and 34, as well as sensing coils L5 L6, L7, and L8, that the viscosity tester of the present invention is adapted to magnetically induce and sense rotational movement of ball 5 within and around fluid placed in testing cup 6, when contained within cup chamber 15, which constitutes a radial gap configuration. Although in this embodiment rotation of ball 5 is preferably maintained in a generally horizontal plane, this particular tester can also be oriented at angles and still produce reliable viscosity measurements. In other embodiments described hereafter, any angle of operation is possible. In some applications, it may be preferable to have testing cup 6 be attached or formed as a permanent part of testing cylinder 10, although having a removable and disposable cup and ball combination will generally be of great advantage.

Figure 6:
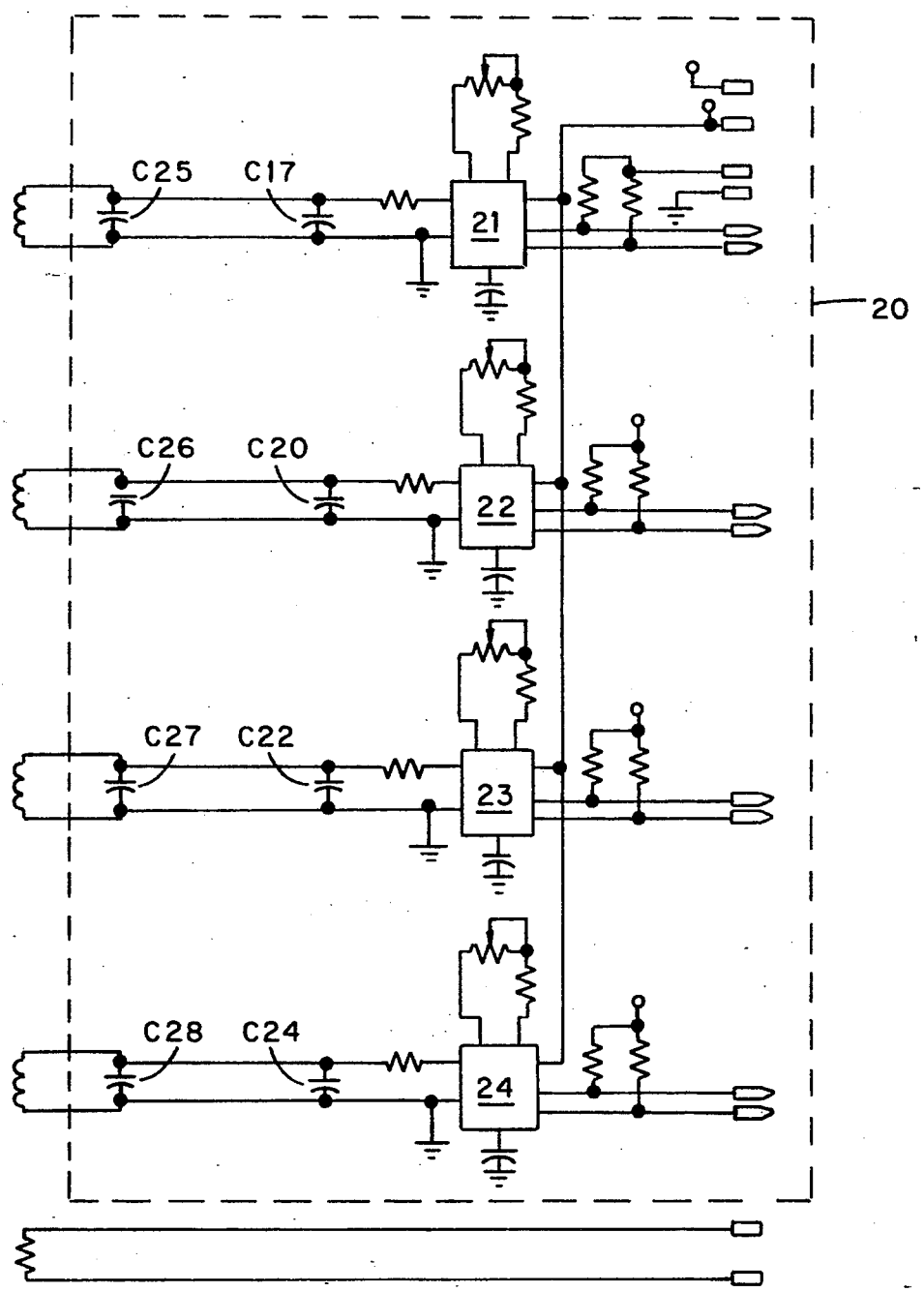
FIG. 6 is a schematic of the sensor circuit of the control and monitoring system.

FIG. 6 schematically illustrates the electronic components which are mounted to sensor board 18, including sensor circuit 20 and sensing coils L5, L6, L7, and LB. As best seen on FIG. 4, each sensing coil L5 L6, L7, and L8 is formed by forming 50 turns of traces on a printed circuit board arranged in a substantially interconnecting circular pattern which conforms to and substantially overlaps bottom wall 17 of cup chamber 15.

Each sensing coils, L6, L7, and L8 is connected to a corresponding eddy current detector 21, 22, 23, and 24, which has associated components which are identical with the exception of resonating capacitors C25, C26, C27, and C28. Looking at first sensing coil L5, for example, parallel capacitors C17 and C25 form with coil L5 a high Q tuned L-C circuit which is coupled through resistor R30 to first eddy current detector 21. The detector 21 includes an oscillator, the frequency of which is determined by the tuned circuit. While eddy current proximity detectors are preferred, one may also use optical detectors, capacity-type detectors, Hall effect sensors, etc. When a magnetic object, such as .testing ball 5, enters the magnetic proximity sensing field of first sensing coil L5, eddy currents are produced in ball 5, thereby detuning or lowering the effective Q factor of the tuned circuit formed by sensing coil L5 and capacitors C25, and C17. This Q loading effect reduces the magnitude of oscillations in first eddy current detector 21. This amplitude change is detected by eddy current detector 21 and converted therein to a proportional DC signal. The change in DC signal is compared to a DC level which is preset by resistor R34 which is, in effect, a sensitivity adjustment for first eddy current current detector 21. When the change in DC voltage caused by the Q loading equals the preset DC level, the outputs of first eddy current detector 21 (represented by output terminals D* and DPROX) are switched, whereby a position indicating signal, either 0 V or 5 V, is sent to electromagnet switching circuit 50 on processor board 19. Each eddy current detector has two outputs, with the second output being inverted. Each eddy current detector 21, 22, 23, and 24 functions identically, being responsive to movement of ball 5 and generating a position indicating signal when ball 5 moves within the proximity sensing field of corresponding sensing coil L5, L6, L7, or L8.

It will be apparent to those skilled in the art from looking at the geometry of sensing coils L5, L6, L7, and L8 as shown on FIG. 4, that the proximity sensing fields of adjacent sensing coils will slightly overlap. This is a desirable result in one embodiment of the viscosity tester so that, as will be discussed below, proper control and movement of ball 5 around testing cup 6 can be maintained. Further, to achieve adequate sensitivity of sensor circuit 20, the pair of capacitors which form the tuned circuit with a corresponding sensing coil, C27 and C25 in conjunction with L5 for example, should be low drift COG types. As shown on FIG. 6, the resonant frequencies of each tuned circuit associated with sensing coils L5, L6, L7, and L8 should be 10 to 20% different from each turned circuit, as established by differing values for capacitors C25, C26, C27, and C28. This helps to prevent undesirable crosstalk and beat frequencies. A preferred range of operation for the oscillator portions of eddy current detectors 21, 22, 23, and 24 is between 0.5 and 1 MHz.

In alternate embodiments, the microprocessor 60 is used to directly monitor the sensing coils L5, L6, L7, and L8, and it is preferred that the sensing field not overlap. In such alternate embodiment, the microprocessor 60 is programmed to energize one and only one magnet at a time.

Figure 5A:
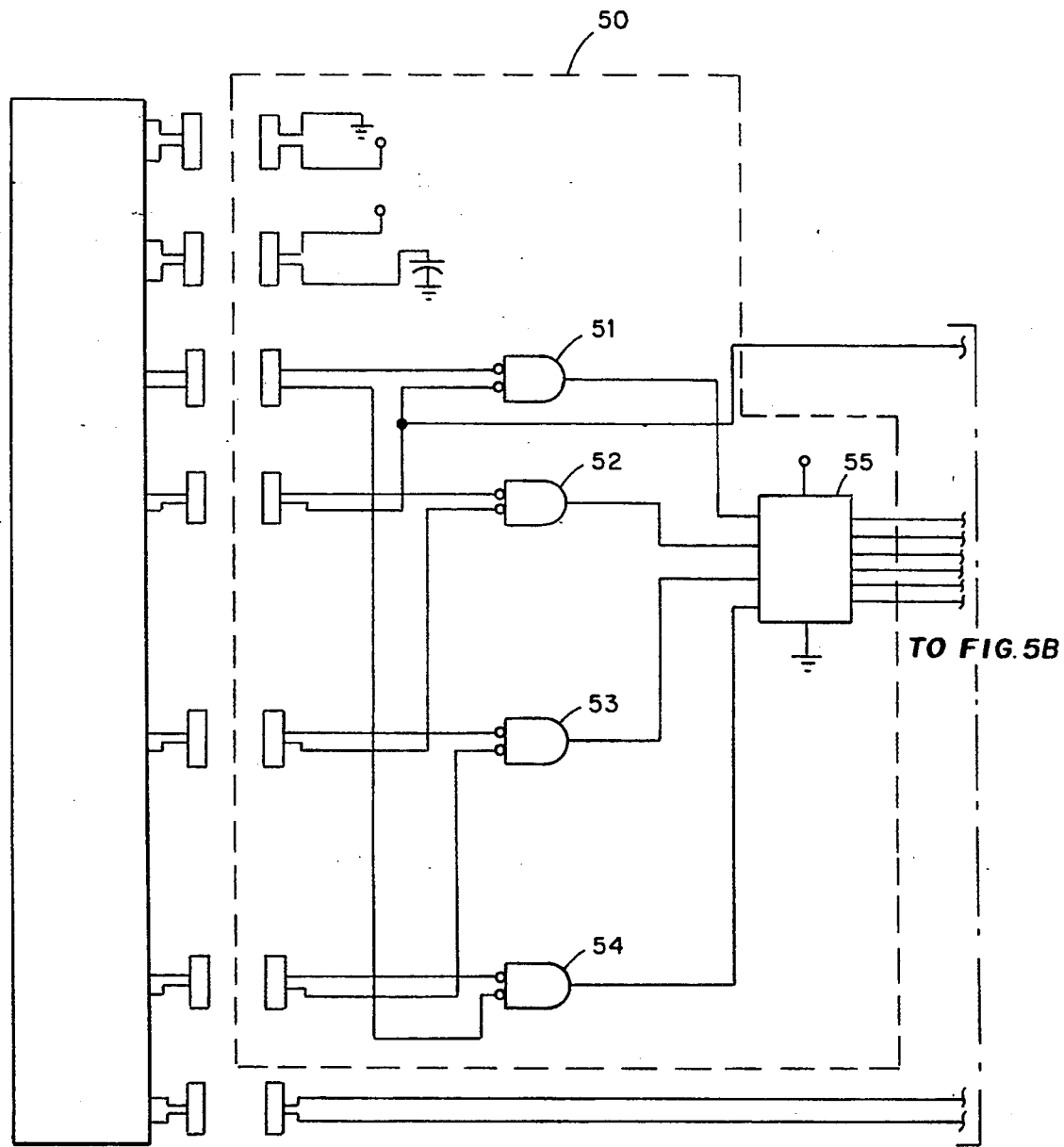
FIG. 5, composed of FIGS. 5A, 5B and 5C, is a schematic of the control and monitoring system of the viscosity tester.
Figure 5B:
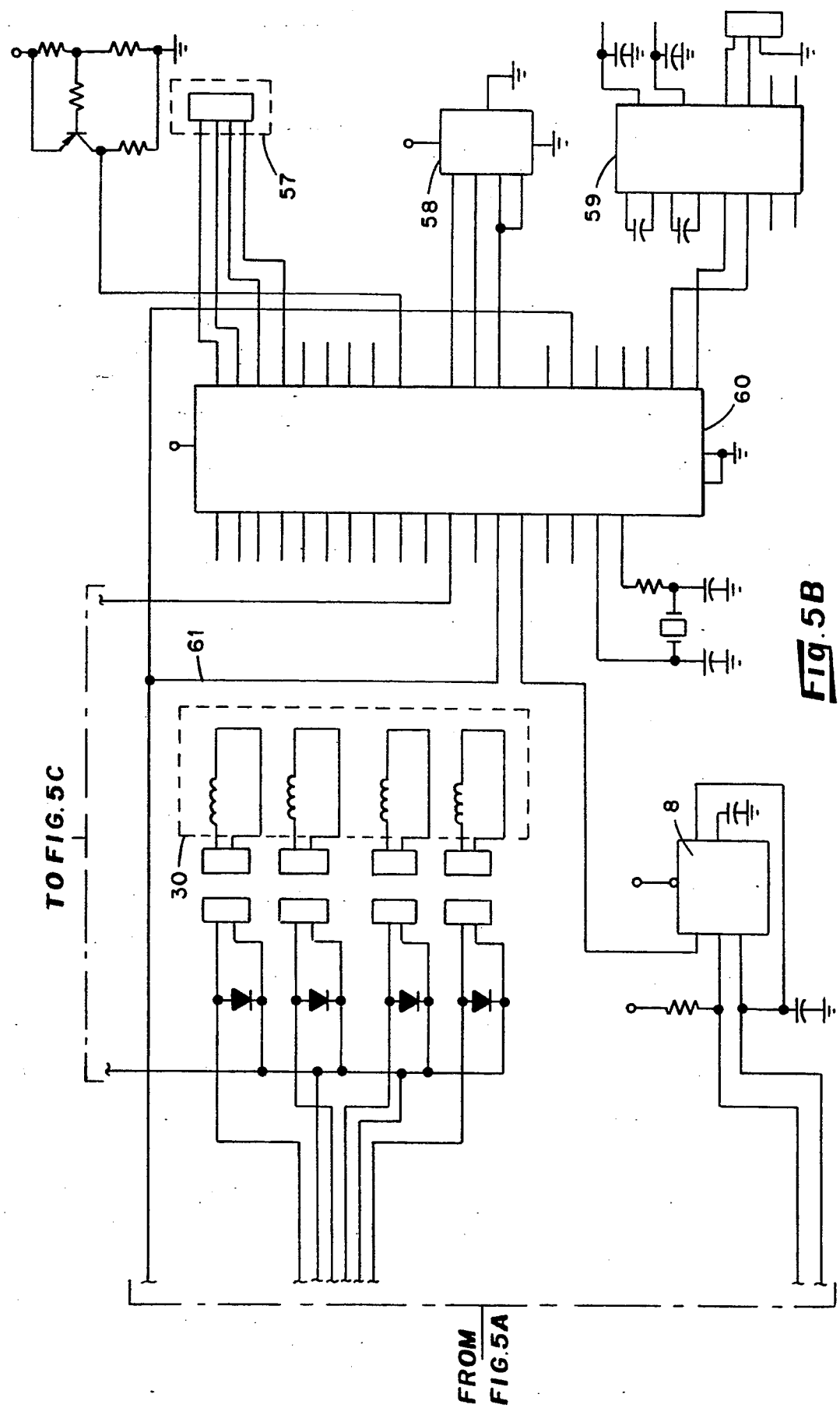
Figure 5C:
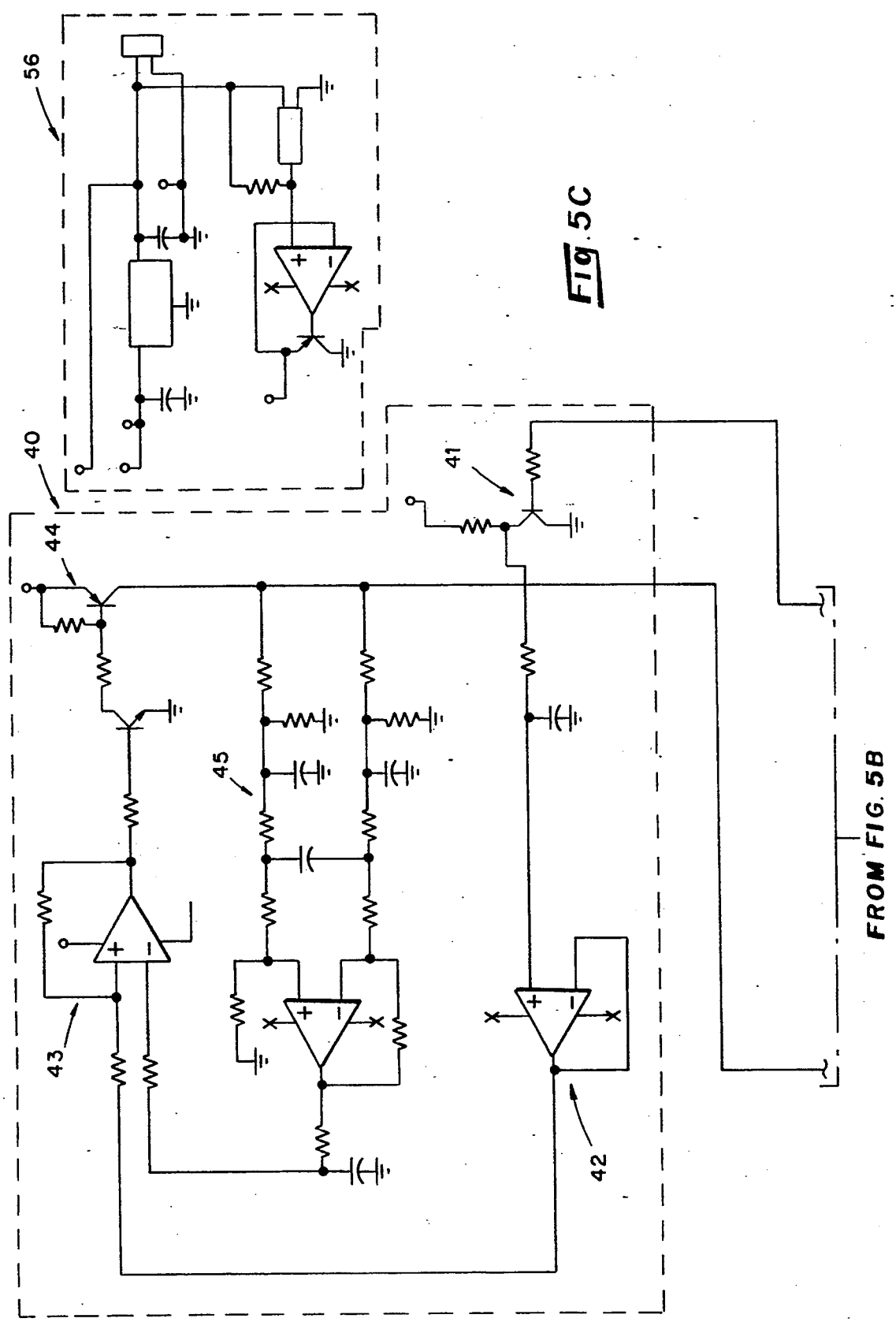

FIG. 5 schematically illustrates the electronic components mounted on processor board 19 and further schematically showing electromagnet assembly 30 (L1, L2, L3 and. L4 on FIG. 5 corresponding to electromagnets 31, 32, 33 and 34 on FIGS. 1 and 2) which are physically separated from but electrically connected to processor board 19. Mounted on processor board 19 and shown on FIG. 5 are microprocessor 60 which is electrically connected to a magnet driver circuit 40, memory unit 58, serial data interface 59, video driver and display 57, and fluid temperature monitoring circuit 8. Power supply 56 supplies operational power for the viscosity tester, including for the circuits located on sensor board 18. In addition, an electromagnet switching circuit 50 is provided on board 19 for receiving test ball position indicating signals from sensor board 18 and using such signals to switch the delivery of magnet activation current from magnet driver circuit 40 to the various electromagnets 31, 32, 33, and 34 of electromagnet assembly 30.

It is important to rotate the ball at a speed that achieves laminar flow. In order to control the velocity of ball 5 within testing cup 6 within a range where laminar flow conditions can prevail, the velocity of ball 5 during the test procedure must be accurately measured and the current used to drive electromagnet assembly 30 be controlled. In furtherance of these objectives, magnet driver circuit 40 is a regulated constant current source in which the current provided to each electromagnet 31, 32, 33, and 34 is directly proportional to and thereby adjustable by a variation in the width of pulses generated at an output of processor 60. This pulse output is presented to isolator transistor stage 41 of magnet driver circuit 40. After passing through an op amp buffer stage 42, the pulses are amplified in pulse amplifier stage 43, the output of which is used in a conventional manner to control the magnitude of current from transistor current source 44. A filtering and feedback stage 45 is connected across precision resistor R24 to monitor the current output of driver circuit 40. Accordingly, if the magnet driver current drops below or above the programmed level, a corresponding adjustment in the gain of amplifier stage 43 is made to reduce or increase the current accordingly.

In a preferred embodiment of the monitor and control circuit of the viscosity tester, the magnitude of the current provided to electromagnet assembly 30 by magnet driver circuit 40 is not infinitely variable. Rather, the velocity of travel of ball 5 around test cup 6 is monitored by processor 60 by counting and timing the position indicating signals generated by sensor circuit 20 and particularly from the output of second eddy current detector 22. In accordance with this pulse timing, if processor 60 determines that the velocity of test ball 5 is too high for laminar flow, processor 60 refers to data stored in a table in memory unit 58, and retrieves predetermined magnet current data associated with the measured pulse timing. Processor 60 uses the retrieved look up table data and in response thereto causes a corresponding reduction in the width of pulses being sent to magnet driver circuit 40. This pulse width reduction produces a decrease in magnet current and, consequently, ball velocity. Only two or three discrete magnet current levels should be necessary to maintain ball velocity within the desired range. A feature of the invention is that by varying the magnetic fields of electromagnets 31, 32, 33 and 34, and thus the ball 5 speed, different shear rates are induced; thus non-Newtonian fluids can be tested. These are fluids whose viscosity changes with shear rates.

Preferably, at least one position indicating signal from sensor circuit 20 is provided through line 61 and is used by processor 60 to generate and communicate data to serial data interface 59, such data being proportional to and therefor useable to calculate the viscosity of the fluid in testing cup 6. Preferably, processor 60, which can be an industry standard microprocessor such as the 17C42P integrated circuit, will be programmed to produce multiple rotations of ball 5 around cup 6 for each test. For example, in one embodiment, 10 to 15 revolutions at approximately two revolutions per second gave an accuracy margin of error of approximately 5%, with a 0.3% repeatability range, for fluid samples having a viscosity between 1 and 5000 centistokes.

The output of serial interface 59, which is preferably a standard RS232 interface device such as the LT1081, is then provided to an external computer which can perform the necessary calculations as described above. Alternatively, processor 60 can be programmed to make this calculation internal to the viscosity tester. The internally calculated data can then be transmitted both through serial interface 59 and at video drive/display unit 57. Those skilled in the art will recognize that an empirically determined viscosity calibration constant will have to be used to correlate the measured viscosity to an absolute viscosity. In one embodiment of the present invention, a calibration constant of 720 centistokes per sec/rev was empirically derived, for an electromagnetic L1–L4 drive current of 1.5 amperes. That is, when an electromagnet L1–L4 drive current of 1.5 amperes was used, and a fluid was used having a viscosity of 720 centistokes, the ball rotates at 1 cycle per second around a cup having an inside diameter of 1¼" using a 9/16" diameter steel ball. Thus, the viscosity meter constant for this condition is 720 centistokes/second/revolution. Using this particular meter in this condition, if a ball was found to travel around the cup at a speed of 0.5 revolutions per second, the viscosity of the sample is calculated to be $720 \div 0.5 = 1440$ centistokes.

For a particular tester constructed according to the present invention, a number of viscosity constants should be empirically determined for a number of overlapping viscosity ranges. For one embodiment of the invention, viscosity constants were empirically determined as shown in the table below. This table represents only one example and the table will vary for different geometries and other variations in a tester.

| Electro-magnet amps | Seconds per Revolution of Ball | Viscosity Meter K Centistokes/sec/rev | Viscosity Range in Centistokes |
| --- | --- | --- | --- |
| .3 | .4 to 3 | 10 | 4 to 30 |
| .7 | .3 to 3 | 80 | 24 to 240 |
| 1.5 | .2 to 4 | 720 | 144 to 2960 |

Thixotropic materials and other non-Newtonian fluids will need to be measured at two speeds to measure the shear rate dependent properties of these materials.

Referring again to FIG. 5, serial data interface unit 59 can be used to receive command signals from an external computer. For example, the operator of the viscosity tester, depending on the type of fluid being tested and the level of accuracy preferred, may wish to adjust the number of rotations of ball 5 within testing cup 6 which are used by the viscosity tester in order to process and average position indicating signals to produce the viscosity measurement.

It will also be apparent to those skilled in the art that the temperature of the fluid to be tested can also be an important parameter to be considered in substantiating the accuracy and reliability of the viscosity measurement and to ensure that the viscosity tester is operating within an appropriate temperature range. Accordingly, processor 60 is programmed to allow the operator to activate one or more electromagnets 31, 32, 33, and 34, with or without testing ball 5 in place, either to heat up the fluid to a preferred temperature and/or to stir the fluid before testing has actually begun. Similarly, as shown on FIG. 3, a fluid temperature sensor 7, preferably a thermistor, is located within test cylinder 10 between sensor board 18 and chamber bottom wall 17. Temperature monitoring circuit 8 (FIG. 5), such as a NE555 voltage-to-frequency integrated circuit device, receives temperature responsive signals from sensor 7, and reports a variation of such temperature as a variation in the frequency of pulses delivered to an input of processor 60. Processor 60 can then count the number of pulses received from temperature monitor 8 and, by reference to a data lookup table in memory unit 58, report the corresponding temperature of the fluid. If desired, processor 60 can be programmed to use the reported temperature from temperature monitor circuit 8 to vary the level of current from magnet drive circuit 40, thereby varying the velocity of test ball 5.

Looking now at FIGS. 5 and 6, the novel method of switching magnet activation current from magnet driver circuit 40 to each individual electromagnet 31, 32, 33, and 34 can be understood. The output of each eddy current detector 21, 22, 23, and 24 is used to control or switch the current to the electromagnet 31, 32, 33, or 34 which geometrically corresponds to each sensing coil L5, L6, L7, and L8. Inverted output from the same eddy current detector is used as well to control the next succeeding electromagnet 31, 32, 33, or 34.

In order to maintain a constant velocity of testing ball 5 through the fluid, with minimal fluctuations and with no dead zones, the proximity sensing fields of coils L5, L6, L7, and L8 overlap at their respective adjacent margins. Further, the viscosity tester of the present invention is designed so that each electromagnet 31, 32, 33, and 34 has sufficient strength to pull the test ball 5 one quarter revolution around test cup 6 through the most viscous fluid intended to be measured in the viscosity tester. Because of the overlap of the proximity sensing fields, electromagnet switching circuit 50 is configured so that only one electromagnet can be activated at one time, even when ball 5 has moved into overlapping sensing fields. Accordingly, separate NAND gates 51, 52, 53, and 54 are provided in switching circuit 50 to control, through current switch 55, the switching of corresponding electromagnets 31, 32, 33, and 34. As previously described, in embodiments that provide sensor signals from L5, L6, L7, and L8 directly to the microprocessor 60, it is preferable to use coils L5-L8 with non-overlapping sensing fields.

Each NAND gate receives a position indicating signal from the eddy current detector associated with its corresponding sensing coil L5, L6, L7, or L8, and an inverted position indicating signal originating from a geometrically preceding sensing coil L5, L6, L7, or L8. Therefore, if testing ball 5 is within the proximity sensing fields of both first sensing coil L5 and adjacent second sensing coil L6, the output of NAND gate 51 prevents current switch 55 from activating first electromagnet 31 until such time as test ball 5 leaves the proximity sensing field of second sensing coil L6. When ball 5 leaves the sensing field of coil L6, the change in position indicating signal, communicated through second NAND gate 52 and current switch 55, deactivates electromagnet 32 and activates electromagnet 31. This process is continuously repeated as ball 5 rotates around testing cup 6. Current switch 55 has multiple outputs as shown, two of which are connected to the output of driver circuit 40 and to the common terminals of electromagnets 31, 32, 33, and 34 of electromagnet assembly 30. The four other outputs of current switch 55 are connected to the separate control terminals of electromagnets 31, 32, 33, and 34. A UDN2878 integrated circuit can be used for this application. Thus, ball position indicating signals from sensor circuit 20 are used directly to control switching of the electromagnets. However, processor 60 could also be programmed to receive all position indicating signals and use them to control magnet switching.

Figure 7:
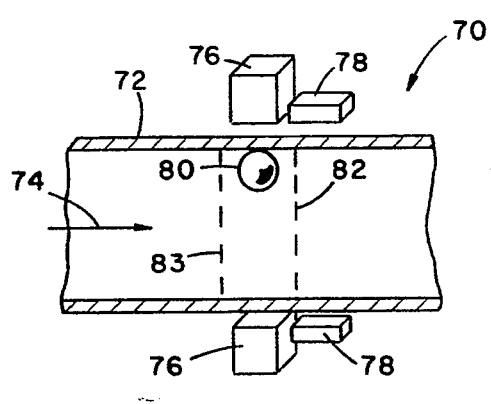
FIG. 7 is a somewhat diagrammatic cross-sectional view of an on-line or in-line viscosity testing of the present invention.

Referring now to FIG. 7, there is shown an alternate embodiment of the present invention. The viscosity tester 70 of FIG. 7 is built into a non-metallic tube 72 in which fluid is flowing as indicated by the arrow 74. For example, the tube 72 may be a non-metallic tube inserted into the process fluid. Electromagnets 76 are spaced around the exterior of the tube 72 and correspond to the electromagnets 31, 32, 33, and 34 shown in the previously described embodiment. Likewise, proximity sensors 78 are spaced around the exterior of the tube 72 and are preferably positioned adjacent to the electromagnets 76. The proximity sensors 78 correspond to the sensor coils L5-L8 described above with reference to previous embodiments. The number of electromagnets 76 and proximity sensors 78 that are spaced around the tube 72 will vary depending upon a particular application, but one may typically use four electromagnets 76 and four sensors 78 equi-distantly spaced around the tube 72. A ferromagnetic ball 80 is disposed inside the tube 72 and is driven in a generally circular orbit around the inside perimeter of the tube 72 by the electromagnets 76. As in the previous embodiment, the sensors 78 detect the position of the ball 80 and the signals from the sensors 78 are used to sequentially switch on the electromagnets 76 to drive the ball 80 around the inside perimeter of the tube 72.

The signals from the sensors 78 are also used by a microprocessor, such as the microprocessor 60 to determine a count that corresponds to the speed of the ball 80 and the viscosity of the fluid within the tube 72.

It will be appreciated that the magnetic force of the magnets 76 will restrain the ball 80 against the flow of the fluid 74. However, for safety purposes, non-metallic screens 82 and 83 are preferably disposed upstream and downstream of the ball 80 so as to capture it within the tube 72 and insure that it remains proximate to the electromagnets 76. Again, however, the screens 82 and 83 are optional and are not absolutely necessary to the functioning of tester 70.

Figure 8:
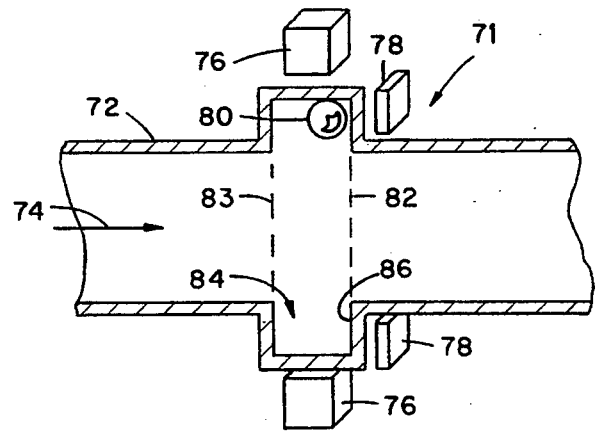
FIG. 8 shows a variation of the embodiment shown in FIG. 7.

Referring to FIG. 8, there is shown a tester 71 that is a variation of tester 70. Tester 71 is identical to tester 70 except that an annular recess 84 is formed inside the tube 72 and projecting outwardly from the tube. The recess 84 creates an annular chamber that is coaxial with the tube 74, and the magnets 76 are mounted around the exterior surface of the recess 84.

In this construction, the recess 84 provides an annular shoulder 86 on the downstream side of the recess 84. The proximity sensors 78 are positioned adjacent and flush against the exterior of the shoulder 86 and the ball 80 is disposed within the recess 84 for rolling on the shoulder 86. The flow of the fluid within the tube 72 will tend to force the ball 80 against the shoulder 86. In this construction, the recess 84 captures the ball 80 and also provides relatively stagnant fluid compared to the rapidly flowing fluid in the center of tube 72. If it is desired to monitor the viscosity of the fluid in a relatively stagnant condition, tester 71 is preferred over tester 70. Again, screens 82 and 83 may be employed to insure that the ball 80 remains captured in a position proximate to the electromagnets From a functional viewpoint, the tester 71 is almost identical to the tester shown in FIG. 1 except that tester 71 is designed to operate at almost any angle of operation. That is, the tester 71 will function with a vertically orbiting ball 80 or a horizontally orbiting ball 80 or with an orbit at any angle in between.

Figure 9:
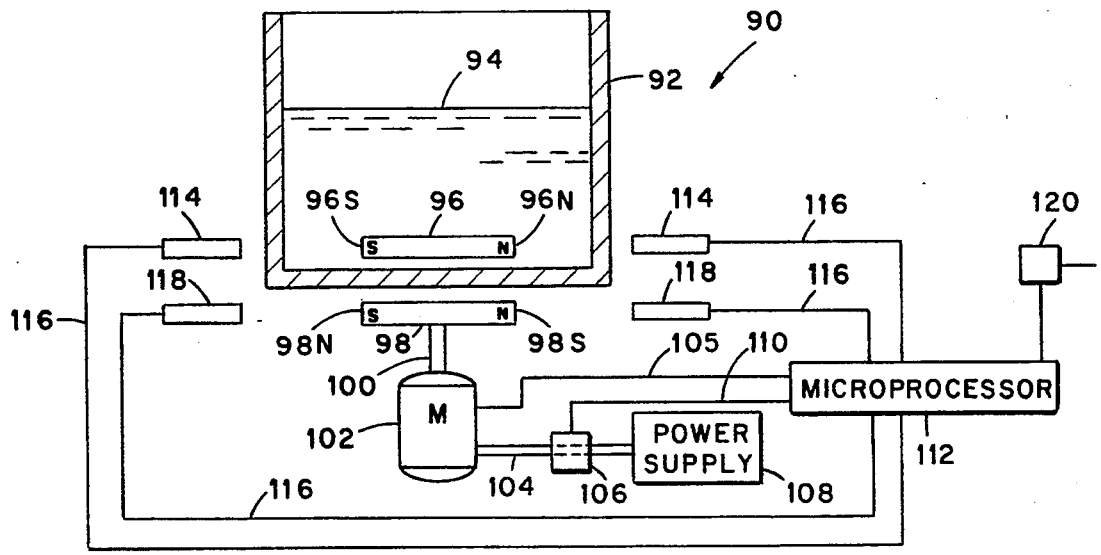
FIG. 9 is a somewhat diagrammatic cross-section view of an embodiment using rotating driver and driven magnets.
Figure 10:
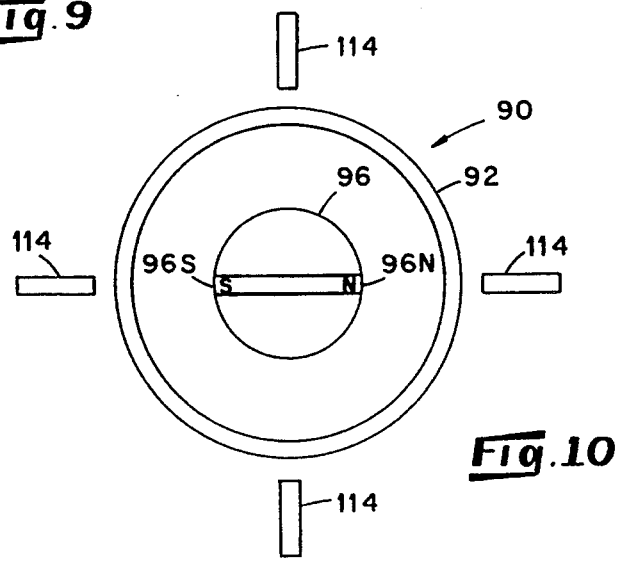
FIG. 10 is a diagrammatic top view of FIG. 9.

Referring now to FIG. 9, there is shown a tester 90 constituting Knother variation or embodiment of the tester shown in FIG. 1. In this embodiment, a cylindrical receptacle 92 contains a fluid 94 whose viscosity will be tested. A free standing permanent magnet 96 is disposed in the fluid 94 resting on the bottom of the receptacle 92. The permanent magnet 96 has a disk shape (flat cylinder) and has a north pole 96N and a south pole 96S. A top view of the tester 90 is shown in FIG. 10, and a comparison of FIGS. 10 and 9 best show the disk shape of the permanent magnet 96. The disk shape of the permanent magnet 96 is chosen to provide a wide range of rotational speeds at which 5 the permanent magnet 96 may be operated and yet maintain laminar flow of the fluid 94. The disk shaped permanent magnet 96 could easily be configured with 4 or 6 or some other number of alternating N-S poles as is commonly done with axial gap, permanent magnet rotors. In fact, the permanent magnet disk 96 could be replaced with a hysteresis drive disk made from an iron alloy which experiences magnetic hysteresis when exposed to Gaussian magnetic fields. Therefore, either an axial gap, permanent magnetic rotor or hysteresis drive rotor are alternate configurations represented by permanent magnet 96.

Disposed below the receptacle 92 is another permanent magnet 98 having a south pole 98S and a north pole 98N. The permanent magnets 98 and 96 have corresponding opposite poles, have axial gap separated by the fluid container, and are magnetically coupled. The permanent magnet 98 is mounted on a shaft 100 that is driven by a motor 102. Thus, as the shaft 100 rotates, the permanent magnets 98 and 96 will likewise rotate in a synchronous manner. To produce a system with only one moving part, one can easily see how the drive system (permanent magnet 98, shaft 100, and motor 102) could be replaced by a wound stator core having poles corresponding to the driven permanent magnet 98 or alternate permanent magnet rotor or hysteresis drive rotor configurations. Therefore, an axial gap motor stator is an alternate configuration for magnet 98, shaft 100, and motor 102.

Current is supplied to the motor 102 through lines 104 from a power supply 108. The current flowing in lines 104 is detected by current sensor 106 and a sensor signal is provided over line 110 to a microprocessor 112. The microprocessor 112 controls the speed of the motor 102 through line 105.

In operation, the microprocessor controls the motor 102 causing it to operate at a constant rotational speed that is selected by the user and may vary according to the particular application. The motor 102 rotates the permanent magnet 98 which in turn rotates the permanent magnet 96 by virtue of the magnetic coupling between the two permanent magnets 96 and 98. The interaction of the permanent magnet 96 with the fluid 94 will tend to prevent the rotation of the permanent magnet 96. The resistance to rotation of the permanent magnet 96 will be directly related to the viscosity of the fluid 94. Thus, the electrical power required to rotate the magnets 98 and 96 at a constant speed will likewise be directly related to the viscosity of the fluid 94. By measuring the electrical current using current sensor 106, one has a measure that corresponds to the power required to operate the motor 102 and, thus, one has a measurement corresponding to the viscosity of the fluid 94.

To calibrate the instrument, a number of fluids having a known viscosity at a known temperature are placed in the receptacle 92 at the known temperature. Then, the motor is operated at a constant known speed and the current is recorded by the microprocessor system 112. In preferred mode of operation, speed range is selected such that flow around the permanent magnet, 96, is laminar, and such that the driven element (96) is lagging the driver (98), and both are in synchronous orbits (e.g., operating at identical speeds). The known viscosity of the fluid is input to the microprocessor system 112 and is recorded in a lookup table in association with the recorded current. By using a number of known fluids at high and low speed ranges (it is essential to use multiple speeds when testing nonNewtonian fluids), a lookup table is generated having numerous current measurements associated with the known viscosity of the fluid that produced the current measurements. When a test fluid is introduced into the receptacle 92, the current is measured by the microprocessor 112 and, using the calibrated lookup table previously described and standard rules of interpolation, a viscosity of the test fluid is determined.

The microprocessor system 112 includes a communication port 120 to enable it to communicate with a computer, such as a standard PC. The port 120 enables the user to connect the microprocessor system 112 to a computer and input information such as the known viscosities that should be associated with particular current measurements. Also, the calibrated viscosities of test fluids may be output to an outside computer through the communication port 120.

In an optional variation of the tester 90, position sensors 114 and 118 may be provided for sensing the position of the magnets 96 and 98 respectively. The sensors 114 and 118 are connected by lines 116 to provide sensor signals to the microprocessor system 112. The sensors 114 are preferably sensor coils that are disposed proximate to the permanent magnet 96 and sense the movement of the poles 96S and 96N. Likewise, the sensors 118 are preferably sensor coils proximate to the permanent magnet 98 for sensing its poles 98S and 98N. It will be understood that FIG. 9 is somewhat diagrammatical and the distances between the sensors 114 and 118 and the permanent magnets 96 and 98, respectively, have been exaggerated for other illustration purposes. It will also be understood that the sensors 114 and 118 may be other types of conventional position sensors. For example, the sensors 114 and 118 could be optical tachometers of conventional design, although optical tachometers might not work well with extremely dark test fluid.

With the provision of the optional sensors 114 and 118, the viscosity of the test fluid may be determined in several different ways. For example, the rotational speed of the magnets 96 and 98 may be held constant and the phase lag between magnet 96 and magnet 98 may be measured. The phase lag will be related to the viscosity of the fluid and again may be correlated to viscosity by the calibration techniques described above.

In an alternate configuration, the microprocessor system 112 is programmed to monitor the current flowing in lines 104 and maintain the current at a constant level. Also, the speed of either magnet 96 or 98 or both is monitored. In this configuration, the rotational speed of the magnets 96 and 98 will be proportional to viscosity and by appropriate calibration techniques, the monitored speed is correlated to viscosity.

The microprocessor system 112 preferably includes a digital display and a keyboard system for directly interacting with the microprocessor. However, these particular components need not be present when the communication port 120 is provided. A host computer connected through the port 120 is also used to collect data, display data, issue commands and provide data to the microprocessor system 112.

Figure 11:
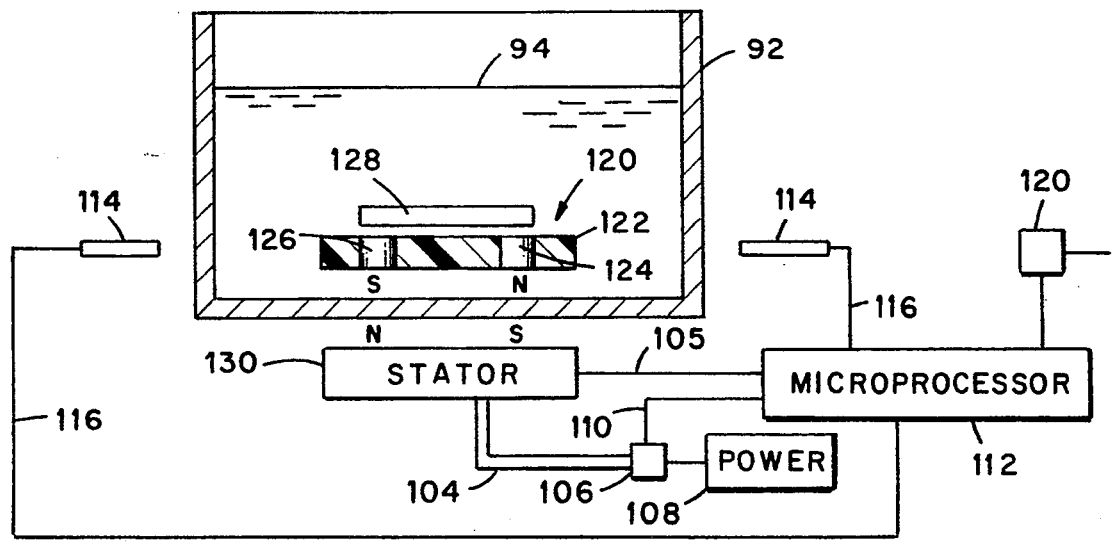
FIG. 11 is a schematic diagram illustrating a variation of the embodiment shown in FIG. 9.
Figure 12:
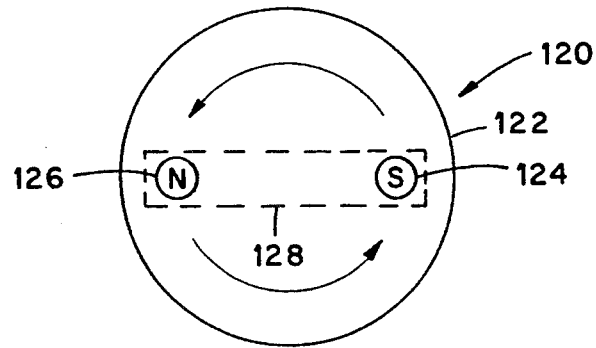
FIG. 12 is a diagrammatic top view of the rotating body shown in FIG. 11.

Referring to FIG. 11, there is shown a partial schematic diagram illustrating a variation of the embodiment of FIG. 9, which was discussed in some detail above. In the embodiment of FIG. 11, the magnet 96 has been replaced with an object 120 of 5 different construction, which includes a non-magnetic, diskshaped body 122 with two (or more) magnets 124 and 126 having polar axes parallel to centerline of rotation and disposed in the body 122 joined by a shunt 128. This embodiment, by showing two (or more) orbiting magnets in a body 122, more clearly illustrates other orbital movement of the magnets, which is best shown in FIG. 12, a top view of the body 122. The orbit is illustrated by arrows 128. The object 120 is driven by a stator 130 that produces a rotating magnetic field having geometry corresponding to magnets 124 and 126. The microprocessor controls the speed of magnetic field rotation of stator 130 to create a controlled rotating magnetic field analogous to the magnetic field produced by the embodiment of FIG. 9. One advantage of using a stator 130 is elimination of moving parts associated with motor 102 and rotating magnet 102. Sensors 124 are provided to monitor the positions of magnets 124 and 126, and the position of the rotating field of stator 130 is dictated by and known to microprocessor 112. Thus, the microprocessor monitors or controls power to the stator 130, the rotational speed of the magnetic field and of magnets 124 and 126, and the lag angle between the magnets 124 and 126 and the rotating magnets field.

It will be appreciated that the permanent magnet 96 of Figs. 9 and 10, and the magnets 124 and 126, correspond to the ball 80 of FIGS. 7 and 8 and the ball 5 of FIGS. 1–3. In each case, the free standing object is being driven in an orbiting pattern within a fluid, and the fluid is resisting the orbital movement. Likewise, the motor 102 and rotating magnet 98, and the stator 130, correspond to the electromagnets 76 of FIGS. 7 and 8 and the electromagnets 31–34 of FIGS. 1–3. In each case, a magnetic force is imposed on an object to drive it in an orbital pattern through a fluid for the purpose of measuring viscosity. To determine viscosity, the various embodiments either measure or control speed, power, and phase lag. In other words, to determine viscosity, one may control the power and phase lag, for example, and measure the speed of the moving object. In the alternative, one may control the speed of the object and phase lag, for example, and measure the power or the current required to impose the appropriate magnetic force to maintain the constant speed. Or, in an alternate embodiment, one may measure the phase lag while controlling speed and power. And, finally, as is the case in the synchronous, axial gap permanent magnet configuration, one may measure the concurrently changing phase lag or drive power or both while holding speed constant. By these examples, the relationship between phase lag, speed and power may be appreciated.

Thus, although there has been described particular embodiments of the present invention of a new and useful viscosity tester, it is not intended that such references be construed as limitations upon the scope of this invention as set forth in the following claims. Further, although there have been described certain dimensions and operational parameters used in the preferred embodiment, it is not intended that such be construed as limitations upon the scope of this invention.

What is claimed is:

1. An apparatus for measuring the viscosity of a fluid, said apparatus comprising:
   a stationary receptacle for containing the fluid;
   a free standing magnetic object on surface a receptacle disposed in the fluid in the receptacle;
   magnet means for producing a magnetic field and imposing a magnetic force on said magnetic object and moving the object through said fluid at a speed and at a lag angle with respect to the magnetic field in a generally orbital pattern in said receptacle to produce at least one parameter corresponding to the viscosity of the fluid;
   control means for controlling at least one of magnetic force, lag angle and speed; and
   sensing means for sensing at least one of the magnetic force, lag angle and speed and for producing a signal corresponding to the viscosity of the fluid.

2. The apparatus of claim 1 wherein said sensing means comprises at least one position sensor for sensing at least one position of the magnetic object as it moves in the generally orbital pattern and produces a position signal whose frequency corresponds to the speed of the magnetic object and the viscosity of the fluid.

3. The apparatus of claim 1 wherein said magnet means further comprises power supply means for supplying power to produce the magnetic force and wherein said sensing means comprises means for measuring the power and producing a signal corresponding to the power required to move the magnetic object through the fluid and also corresponding to the viscosity of the fluid, whereby magnetic force is measured by measuring said power.

4. The apparatus of claim 1 wherein said receptacle comprises a testing cup and a cup chamber adapted for releasably supporting said testing cup proximate to said magnet means and to said sensing means, whereby said testing cup is separate and removable from said apparatus.

5. The apparatus of claim 1, said magnet means comprising a plurality of separately operable electromagnets arranged in a generally circular pattern around said receptacle.

6. The apparatus of claim 5 further comprising:
   said sensing means for sensing the position of the magnetic object and producing a position signal; and
   said control means for sequentially activating said electromagnets, one electromagnet at one time; and in which said control means uses the position signal from the detector which senses the position of the magnetic object in order to determine when to sequentially activate the next electromagnet.

7. The apparatus of claim 1 wherein said magnet means comprises a stator disposed proximate to said object for producing a moving magnetic field to drive said object in the orbital pattern.

8. The apparatus of claim 1 further comprising said control means for controlling the magnetic force on said magnetic object and limiting said object velocity within a range where laminar flow conditions are maintained.

9. The apparatus of claim 1, said sensing means comprising a plurality of proximity sensors arranged in a generally circular pattern proximate to said receptacle, each of said proximity sensors having a proximity sensing field associated therewith, said sensing fields responsive to said object within said proximity sensing fields.

10. The apparatus of claim 9 wherein said proximity sensing fields associated with adjacent said proximity sensors partially overlap.

11. The apparatus of claim 1 further comprising a temperature sensor for sensing the temperature of the fluid and generating a temperature signal.

12. The apparatus of claim 11 further comprising said control means responsive to the temperature signal for energizing the electromagnet means to produce heat for heating the fluid to a predetermined temperature.

13. The apparatus of claim 1 wherein said receptacle comprises a cylindrical well permanent and integral to the apparatus.

14. The apparatus of claim 1 wherein said magnetic object comprises a spherical magnetic ball.

15. The apparatus of claim 1 wherein said magnetic object comprises a disk-shaped permanent magnet having a diameter and an axis perpendicular to said diameter, said disk shaped permanent magnet having north and south poles disposed in plane of magnet on opposite ends of said diameter.

16. The apparatus of claim 1 wherein said stationary receptacle comprises a tube having first and second open ends for containing the fluid and allowing the fluid to flow from the first to the second end, 17. The apparatus of claim 1 wherein said receptacle further comprises a surface between said magnet means and said free standing magnetic object and imposes a radial gap therebetween.

18. The apparatus of claim 1 wherein said receptacle further comprises a surface between said magnet means and said free standing magnetic object and imposes an axial gap therebetween.

19. The apparatus of claim 1 wherein:
said free standing magnetic object comprises:
a permanent magnet configuration having at least one north pole and at least one south pole which orbit a centerline under the influence of said magnet means; and
an axial gap surface separating the magnet means from the free standing object;
said magnet means comprises a magnet driver for producing a rotating magnetic field, imposing a magnetic force on said free standing magnet and moving said free standing magnet through said fluid in a generally orbital pattern in said receptacle, whereby the north and south poles of said free standing magnet orbit about the center of said free standing magnet.

20. The apparatus of claim 1 further comprising:
said control means for controlling said magnet means to produce multiple magnetic forces insequence to move said object at multiple speeds sequentially; and said sensing means for sensing and determining the speed of said object at each of the multiple speeds, whereby the viscosity of non-Newtonian fluids may be determined from the multiple speeds.

21. The apparatus of claim 20 wherein:
said magnet driver comprises a second magnet disposed on the outside of said receptacle and magnetically coupled to said permanent magnet, an electric motor for rotating said second magnet to produce the rotating magnetic field at a selected angular velocity, and a power supply for supplying an electric current to said motor; and
said sensing means comprises a current sensor for sensing the current supplied to said motor while rotating said permanent magnet and said second magnet and producing an output signal corresponding to the magnetic force and the viscosity of the fluid.

22. The apparatus of claim 20 wherein:
said magnet means comprises a second magnet disposed on the outside of said receptacle and magnetically coupled to said permanent magnet, an electric motor for rotating said second magnet to produce the rotating magnetic field, and a power supply for supplying an electric current to said motor; and
said sensing means comprises a first position sensor for sensing the position of the permanent magnet while it is rotating and producing a first sensor signal, a second position sensor for sensing the position of the second magnet while it is rotating and producing a second sensor signal, and a phase comparator for receiving the first and second sensor signals, determining the phase lag between the permanent magnet and said second magnet, and producing an output signal based on the phase lag at a selected speed of said object and power supply output level corresponding to the viscosity of the fluid.

23. An apparatus for measuring the viscosity of a fluid, said apparatus comprising:
a receptacle for containing the fluid;
a free standing magnetic object on surface or receptacle disposed in the fluid in the receptacle;
magnet means for producing and imposing a magnetic force on said magnetic object and moving the magnetic object through said fluid in a generally orbital pattern in said receptacle to produce at least one parameter corresponding to the viscosity of the fluid;
sensing means for sensing the parameter and producing a signal corresponding to the viscosity of the fluid, said sensing means having at least one position sensor for sensing the magnetic object at a sensed position as the magnetic object moves in the generally orbital pattern and repetitively producing a position signal that corresponds to the speed of the magnetic object and the viscosity of the fluid, whereby said parameter being sensed is the speed of the magnetic object; and
processing means responsive to the position signal for counting each time said object passes the sensed position during a predetermined period of time to produce a count corresponding to the number of times the magnetic object completes the orbital pattern during said period of time.

24. A viscosity tester for fluid comprising:

a centrally disposed chamber for containing the fluid, having a cylindrical side wall and a circular bottom wall defining a chamber said bottom wall having a perimeter at side wall junction;

a magnetic object for being disposed in said chamber in said fluid;

a plurality of electromagnets mounted in positions spaced around and proximate to said chamber side wall;

a plurality of proximity sensing coils mounted proximate to said chamber bottom wall, each proximity sensing coil having a sensing field and producing a sensor signal when said magnetic object is within said sensing field, a unique one of said proximity sensors being associated with each one of said electromagnets;

a power supply;

a control system interconnected with said power supply, said electromagnets and said proximity sensors for selectively sequentially energizing said electromagnets, for energizing a particular one of said electromagnets in response to a sensor signal from the proximity sensor coil that is uniquely associated with the particular one of said electromagnets, for imposing magnetic forces on said object to urge said magnetic object in a generally circular path along the cylindrical side wall and proximate to said perimeter; and means for producing an output signal corresponding to the viscosity of said fluid based on at least one of said sensor signals.

25. A method for measuring the viscosity of a test fluid comprising:

disposing a free standing magnetic object on a surface in the fluid;

producing and imposing a magnetic force on said magnetic object and moving the magnetic object through said fluid in a generally orbital pattern to produce at least one parameter corresponding to the viscosity of the fluid; and repetitively sensing said parameter and producing a signal corresponding to the viscosity of the fluid, 26. The method of claim 25 wherein said repetitively sensing is a step that comprises sensing the position of the magnetic object as it moves in said orbital pattern and producing an output signal corresponding to the speed of the magnetic object and the fluid viscosity.

27. The method of claim 25 wherein said repetitively sensing is a step that comprises sensing a lag between the position of the magnetic object and the magnetic force.

28. The method of claim 25 wherein said repetitively sensing is a step that comprises sensing a magnitude of electrical power corresponding to magnetic force which is required to move the magnetic object through the fluid.

29. The method of claim 25 further comprising:

monitoring the speed of the magnetic object as it moves through the fluid;

comparing the speed of the magnetic object to a reference speed, said reference speed being chosen to be equal to less than the speed at which non-laminar flow conditions are created by the moving object; and reducing the magnitude of the magnetic force imposed on said magnetic object when the speed of the magnetic object is greater than the reference speed in order to maintain laminar flow conditions.

30. The method of claim 25 further comprising:

measuring the viscosity and temperature of a reference fluid to produce a reference viscosity and temperature measurement;

measuring the viscosity and temperature of a sample fluid to produce a sample viscosity and temperature measurement; and comparing the sample viscosity and temperature measurements to the reference viscosity and temperature measurements to produce a relative viscosity measurement of the sample fluid.

* * * * *

UNITED STATES PATENT AND TRADEMARK OFFICE
CERTIFICATE OF CORRECTION

PATENT NO. : 5,394,739

DATED : March 7, 1995

INVENTOR(S) : Raymond E. Garvey, III, et al.

It is certified that error appears in the above-indentified patent and that said Letters Patent is hereby corrected as shown below:

Title page, item [21]
Appln. No.: delete "254,060" and insert -- 254,159 --.

Col. 2, line 22, delete "frictional-and" and insert -- frictional and --.

Col. 4, line 58, delete "L5-hereinafter" and insert -- L5-L8 hereinafter --.

Col. 5, line 56, delete "LB" and insert -- L8 --.

Col. 5, line 62, after "coils," insert -- L5".

Col. 6, line 40, after "coil," delete "C27" and insert -- C17 --.

Col. 8, line 23, after "of" delete "1¼" and insert -- 1-1/8 --.

Col. 9, line 25, after "coil" delete "LS" and insert -- L5--.

UNITED STATES PATENT AND TRADEMARK OFFICE
CERTIFICATE OF CORRECTION

PATENT NO. : 5,394,739 Page 2 of 2
DATED : March 7, 1995
INVENTOR(S) : Raymond E. Garvey, III, et al.

It is certified that error appears in the above-indentified patent and that said Letters Patent is hereby corrected as shown below:

Col. 11, line 2, after "electromagnets" insert -- 76. --

Col. 11, line 10, delete "Knother" and insert -- another --.

Col. 11, line 21, after "which" delete "5".

Col. 13, line 19, after "of" delete "5".

Col. 13, line 31, after "processor" insert -- 112 --.

Col. 13, line 36, delete "124" and insert -- 114 --.

Signed and Sealed this

Nineteenth Day of November, 1996

Attest:

BRUCE LEHMAN

*Attesting Officer*     *Commissioner of Patents and Trademarks*